United States Patent [19]

Looker

[11] Patent Number: 4,560,683

[45] Date of Patent: Dec. 24, 1985

[54] CEPHALOSPORIN ANTIBIOTICS

[75] Inventor: Brian E. Looker, Greenford, England

[73] Assignee: Glaxo Group Limited, London, England

[21] Appl. No.: 509,043

[22] Filed: Jun. 29, 1983

[30] Foreign Application Priority Data

Jun. 30, 1982 [GB] United Kingdom ............ 8218874
Aug. 2, 1982 [GB] United Kingdom ............ 8222236

[51] Int. Cl.$^4$ .................. A61K 31/545; C07D 501/24
[52] U.S. Cl. .................................. 514/202; 544/22
[58] Field of Search ................ 544/22, 28; 424/246

[56] References Cited

U.S. PATENT DOCUMENTS

| | | |
|---|---|---|
| 3,946,002 | 3/1976 | Davison .................... 424/246 |
| 3,966,717 | 6/1976 | Cook et al. ................ 424/246 |
| 4,033,950 | 7/1977 | Cook et al. ................ 424/246 |
| 4,098,888 | 7/1978 | Ochiai et al. ............... 544/27 |
| 4,162,360 | 7/1979 | Bradshaw et al. .......... 424/246 |
| 4,166,115 | 8/1979 | Takaya et al. .............. 424/246 |
| 4,278,671 | 7/1981 | Ochiai et al. ............... 544/27 |
| 4,278,793 | 7/1981 | Durckheimer et al. ...... 544/27 |

FOREIGN PATENT DOCUMENTS

| | | |
|---|---|---|
| 0025199 | 3/1981 | European Pat. Off. . |
| 0037797 | 12/1981 | European Pat. Off. . |
| 2029824 | 3/1980 | United Kingdom . |
| 1584398 | 2/1981 | United Kingdom . |

OTHER PUBLICATIONS

Morrison and Boyd, "Organic Chemistry", 3rd Ed., pp. 673, 675, 746 & 747.

*Primary Examiner*—Donald G. Daus
*Assistant Examiner*—Robert Benson
*Attorney, Agent, or Firm*—Bacon & Thomas

[57] ABSTRACT

Cephalosporin antibiotics of general formula

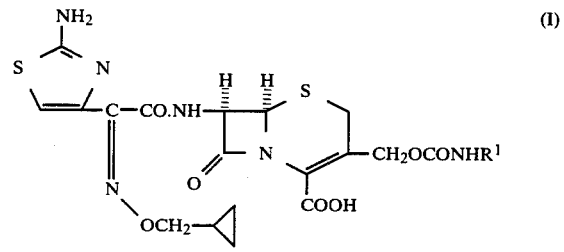

(wherein $R^1$ represents a hydrogen atom or a methyl or 2-chloroethyl group) and non-toxic salts and non-toxic metabolically labile esters thereof. The compounds exhibit broad spectrum antibiotic activity and have high activity against both Gram-positive and Gram-negative organisms, including many β-lactamase producing strains. Processes for the preparation of the compounds and pharmaceutical compositions containing them are described.

5 Claims, No Drawings

CEPHALOSPORIN ANTIBIOTICS

This invention relates to improvements in or relating to cephalosporins. More particularly it relates to new cephalosporin compounds and derivatives thereof having valuable antibiotic activity.

The cephalosporin compounds in this specification are named with reference to "cephem" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both Gram-positive and Gram-negative microorganisms, and a significant amount of research has been directed to the development of various types of broad spectrum cephalosporin antibiotics.

Thus, for example in our British Patent Specification No. 1,399,086, we describe a novel class of cephalosporin antibiotics containing a 7β-(α-etherified oximino)acylamido group, the oximino group having the syn configuration. This class of antibiotic compounds is characterized by high antibacterial activity against a range of Gram-positive and Gram-negative organisms coupled with particularly high stability to β-lactamases produced by various Gram-negative organisms.

The discovery of this class of compounds has stimulated further research in the same area in attempts to find compounds which have improved properties, for example against particular classes of organisms especially Gram-negative organisms.

Our British Patent Specification No. 1453049 discloses, inter alia, the compound (6R,7R)-3-carbamoyloxymethyl-7-[(Z)-2-(fur-2-yl)-2-methoxyiminoacetamido]ceph-3-em-4-carboxylic acid, which is known by the approved name of "cefuroxime".

In British Patent Specification No. 1,604,971 a wide variety of cephalosporin antibiotics are disclosed in which the 7β-position side-chain may be selected from, inter alia, a 2-(2-aminothiazol-4-yl)-2-(etherified oxyimino)acetamido group, in which the etherifying group, amongst very many possible meanings, may be an alkyl group substituted by a cycloalkyl group, although there is no specific exemplification of compounds having such a group. The 3-position group may also be selected from a large number of alternatives and a possible 3-substituent is an optically substituted carbamoyloxymethyl group. Other cephalosporin compounds possessing a 2-(2-aminothiazol-4-yl)-2-(etherified oxyimino)acetamido group in the 7β-position are disclosed in, for example, British Patent Specification Nos. 1584398 and 2029824.

We have now discovered that by the selection of a (Z)-2-(2-aminothiazol-4-yl)-2-cyclopropylmethoxyiminoacetamido group at the 7β-position in combination with certain particular groups at the 3-position, cephalosporin compounds having particularly advantageous activity (described in more detail below) against a wide range of commonly encountered pathogenic organisms may be obtained.

Accordingly, we provide cephalosporin antibiotics of the general formula (I)

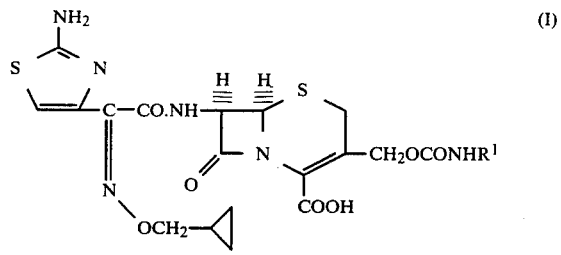

wherein $R^1$ represents a hydrogen atom or a methyl or 2-chloroethyl group, and non-toxic salts and non-toxic metabolically labile esters thereof.

The compounds according to the invention are syn isomers. The syn isomeric form is defined by the configuration of the

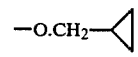

group with respect to the carboxamido group. In this Specification, the syn configuration is denoted structurally as

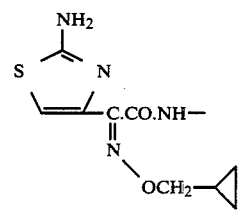

It will be understood that since the compounds according to the invention are geometric isomers, some admixture with the corresponding anti isomer may occur.

The invention also includes within its scope the solvates (especially the hydrates) of the compounds of formula (I) and of their non-toxic salts. It also includes within its scope non-toxic salts and solvates of the non-toxic metabolically labile esters of the compounds of formula (I). It will be appreciated that the solvates should be pharmacologically acceptable.

The compounds according to the present invention may exist in tautomeric forms (for example in respect of the 2-aminothiazolyl group) and it will be understood that such tautomeric forms, e.g. the 2-iminothiazolinyl form, are included within the scope of the invention.

The compounds according to the invention exhibit broad spectrum antibiotic activity both in vitro and in vivo. They have high activity against both Gram-positive and Gram-negative organisms, including many β-lactamase producing strains. The compounds also possess high stability to β-lactamases produced by a range of Gram-negative and Gram-positive organisms.

Compounds according to the invention have been found to exhibit high activity against strains of *Staphylococcus aureus, Staphylococcus epidermidis* and Streptococcus species including penicillinase producing strains of these Gram-positive bacteria. This is coupled with high activity aginst various members of the Enterobacteriaceae (e.g. strains of *Escherichia coli, Klebsiella pneumoniae, Enterobacter cloaecae, Serratia marcescens, Proteus mirabilis* and indole-positive Proteus organisms such as *Proteus vulgaris, Proteus morganii* and Providence species), and strains of *Haemophilus influenzae* and *Acinetobacter calcoaceticus* as well as good activity against Pseudomonas species. This combination of high activity against Gram-positive organisms with high activity against Gram-negative organisms possessed by the compounds of the invention is particularly unusual.

Non-toxic salt derivatives which may be formed by reaction of the carboxyl group present in the compounds of formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenylethylbenzylamine, dibenzylethylenediamine, ethanolamine, diethanolamine and N-methylglucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of the compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Non-toxic metabolically labile ester derivatives which may be formed by esterification of the carboxyl group in the parent compound of formula (I) include acyloxyalkyl esters, e.g. lower alkanoyloxy-methyl or -ethyl esters such as acetoxy-methyl or -ethyl or pivaloyloxymethyl esters, and alkoxycarbonyloxyalkyl esters, e.g. lower alkoxycarbonyloxyethyl esters such as an ethoxycarbonyloxyethyl ester. In addition to the above ester derivatives, the present invention includes within its scope the compounds of formula (I) in the form of other physiologically acceptable equivalents, i.e. physiologically acceptable compounds which, like the metabolically labile esters, are converted in vivo into the parent antibiotic compound of formula (I).

These and other salt and ester derivatives such as the salts with toluene-p-sulphonic and methanesulphonic acids and the esters with t-butyl or diphenylmethyl esterifying groups may be employed as intermediates in the preparation and/or purification of the present compounds of formula (I), for example in the processes described below.

A preferred compound according to the invention is (6R,7R)-7-[(Z)-2-(2-aminothiazol-4-yl)-2-cyclopropylmethoxyiminoacetamido]-3-carbamoyloxymethylceph-3-em-4-carboxylic acid and the non-toxic salts and non-toxic metabolically labile esters thereof.

The compounds of the invention may be used for treating a variety of diseases caused by pathogenic bacteria in human beings and animals, such as respiratory tract infections and urinary tract infections.

According to another embodiment of the invention we provide a process for the preparation of an antibiotic compound of general formula (I) as hereinbefore defined or a non-toxic salt or non-toxic metabolically labile ester thereof which comprises forming a compound of formula

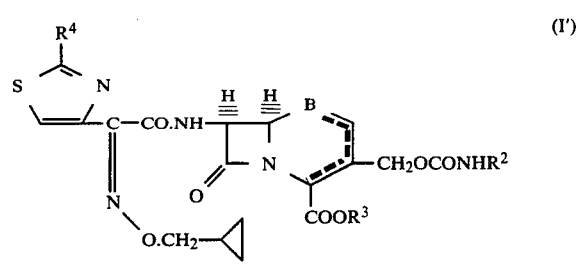

(wherein $R^2$ is the group $R^1$ as defined above or an N-protecting group, e.g. a labile group such as an acyl group, especially a lower alkanoyl group such as acetyl, a halo-substituted lower alkanoyl group such as mono-, di- or trichloroacetyl, a chlorosulphonyl or bromosulphonyl group, or a halogenated alkoxycarbonyl group such as 2,2,2-trichloroethoxycarbonyl; $R^3$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1 to 20 carbon atoms); $R^4$ is an amino or protected amino group; B is >S or >S→O ($\alpha$- or $\beta$-); and the dotted line bridging the 2-, 3- and 4-positions indicates that the compound is a ceph-2-em or ceph-3-em compound) or a salt thereof, by (A) acylating a compound of the formula

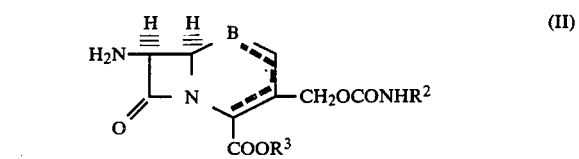

(wherein $R^2$, $R^3$, B and the dotted line are as defined above) or a salt, e.g. an acid addition salt (formed with, for example, a mineral acid such as hydrochloric, hydrobromic, sulphuric, nitric or phosphoric acid or an organic acid such as methanesulphonic or toluene-p-sulphonic acid) or a 7-N-silyl derivative thereof, with an acid of formula (wherein $R^4$ is as defined above) or a salt thereof, or with an acylating agent corresponding thereto; or (B) reacting a compound of formula

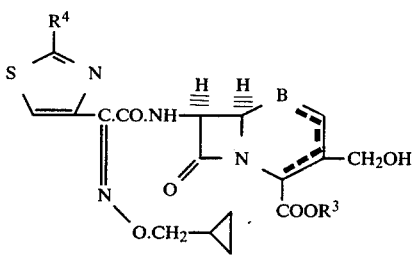

(wherein $R^3$, $R^4$, B and the dotted line are as defined above) or a salt thereof, with an acylating agent serving to form the group —CH$_2$OCONHR$^2$ (wherein $R^2$ is as defined above) at the 3-position; whereafter, if necessary and/or desired in each instance, any of the following reactions, in any appropriate sequence, are carried out:

(i) conversion of a $\Delta^2$-isomer into the desired $\Delta^3$-isomer,
(ii) reduction of a compound wherein B is >S→O to form a compound wherein B is >S,
(iii) conversion of a carboxyl group into a non-toxic metabolically labile ester function,
(iv) formation of a non-toxic salt, and
(v) removal of any carboxyl blocking and/or N-protecting groups.

The above reactions (i) to (v) may be carried out in conventional manner.

In the above-described process (A), the starting material of formula (II) is preferably a compound wherein B is >S and the dotted line represents a ceph-3-em compound.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Acylations employing acid halides may be effected in aqueous and non-aqueous reaction media, conveniently at temperatures of from −50° to +50° C., preferably −40° to +30° C., if desired in the presence of an acid binding agent. Suitable reaction media include aqueous ketones such as aqueous acetone, aqueous alcohols such as aqueous ethanol, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids of formula (III) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorous acids), sulphuric acid or aliphatic or aromatic sulphonic acids (for example toluene-p-sulphonic acid). An activated ester may conveniently be formed in situ using, for example, 1-hydroxybenzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. methylene chloride, tetrahydrofuran, dimethylformamide or acetonitrile.

An alternative method of activation is, for example, by reacting an acid of formula (III) with a solution or suspension preformed by adding a carbonyl halide, in particular oxalyl chloride or phosgene, or a phosphoryl halide such as phosphorus oxychloride to a solvent such as a halogenated hydrocarbon, for example methylene chloride, containing a lower acyl tertiary amide such as N,N-dimethylformamide. The activated form of the the acid of formula (III) may then be reacted with a 7-amino compound of formula (II) in a suitable solvent or mixture of solvents for example a halogenated hydrocarbon e.g. dichloromethane. The acylation reaction may conveniently be effected at temperatures of from −50° to +50° C, preferably −40° to +30° C., if desired in the presence of an acid binding agent, for example as described above (e.g. dimethylaniline).

If desired, the above acylation reactions may be carried out in the presence of a catalyst such as 4-dimethylaminopyridine.

The acids of formula (III) and acylating agents corresponding thereto may, if desired, be prepared and employed in the form of their acid addition salts. Thus, for example, acid chlorides may conveniently be employed as their hydrochloride salts, and acid bromides as their hydrobromide salts.

Carbamoylation of 3-hydroxymethyl compounds of formula (IV) may be effected by conventional methods using suitable carbamoylating agents. Such suitable carbamoylating agents include isocyanates of formula $R^5$.NCO (wherein $R^5$ is a labile substituent group or a methyl or 2-chloroethyl group), to give a compound containing a 3-position substituent having the formula CH$_2$O.CONHR$^5$ (wherein $R^5$ has the above defined meaning). The labile group $R^5$ may subsequently be cleaved, e.g. by hydrolysis, to form a 3-carbamoyloxymethyl group. Examples of labile groups $R^5$ which are readily cleavable upon subsequent treatment include those labile groups hereinbefore given as examples of the group $R^2$. Such labile groups may generally be cleaved by acid or base catalysed hydrolysis (e.g. by base catalysed hydrolysis using sodium bicarbonate).

The reaction product may be separated from the reaction mixture, which may contain, for example, unchanged cephalosporin starting material and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding desired $\Delta^3$-derivative by, for example, treatment of the Δ²-ester with a base, such as pyridine or triethylamine.

A ceph-2-em reaction product may also be oxidised to yield the corresponding ceph-3-em-1-oxide, for example by reaction with a peracid, e.g. peracetic or m-chloroperbenzoic acid; the resulting sulphoxide may subsequently be reduced as described hereinafter to yield the corresponding desired ceph-3-em sulphide.

Where a compound is obtained in which B is $>S \rightarrow O$ this may be converted into the corresponding sulphide by, for example, reduction of the corresponding acyloxysulphonium or alkoxysulphonium salt prepared in situ by reaction with e.g. acetyl chloride in the case of an acetoxysulphonium salt, reduction being effected by, for example, sodium dithionite or by iodide ion as in a solution of potassium iodide in a water-miscible solvent e.g. acetic acid, acetone, tetrahydrofuran, dioxan, dimethylformamide or dimethylacetamide. The reaction may be effected at a temperature of from $-20°$ to $+50°$ C.

Metabolically labile ester derivatives of the compounds of formula (I) may be prepared by reacting a compound of formula (I) or a salt or protected derivative thereof with the appropriate esterifying agent such as an acyloxyalkyl halide or alkoxycarbonyloxyalkyl halide (e.g. iodide) conveniently in an inert organic solvent such as dimethylformamide or acetone, followed, where necessary, by removal of any protecting groups.

Base salts of the compounds of formula (I) may be formed by reacting an acid of formula (I) with an appropriate base. Thus, for example, sodium or potassium salts may be prepared using the respective 2-ethylhexanoate or hydrogen carbonate salt. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation or chromatography.

For use as starting materials for the preparation of compounds of general formula (I) according to the invention, compounds of general formula (III) and the amide forming derivatives thereof such as acid halides and anhydrides corresponding thereto in their syn isomeric form or in the form of mixtures of the syn isomers and the corresponding anti isomers containing at least 90% of the syn isomer are preferably used.

Acids of formula (III) and their derivatives may be prepared by etherification of a compound of formula

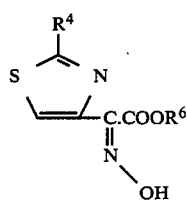
(VI)

(wherein $R^4$ is as hereinbefore defined and $R^6$ represents hydrogen or a carboxyl blocking group) or a salt thereof, by selective reaction with a compound of general formula

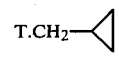
(VII)

(wherein T is halogen, such as chloro, bromo or iodo; sulphate; or sulphonate, such as tosylate), followed by removal of any carboxyl blocking group $R^6$. Separation of isomers may be effected either before or after such etherification. The etherification reaction is conveniently carried out in the presence of a base, e.g. potassium carbonate or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oxyimino group is substantially unchanged by the etherification reaction. When the compound of formula (VI) is employed in the form of a free acid or a salt with a base, the etherification reaction is generally carried out in the presence of a strong base, e.g. potassium t-butoxide, sufficient base being added to form a dianion. Furthermore, the reaction should be effected in the presence of a base if an acid addition salt of a compound of formula (VI) is used, the amount of base being sufficient to neutralise rapidly the acid in question.

Acids of formula (III) may also be prepared by reaction of a compound of formula

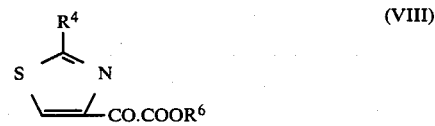
(VIII)

(wherein $R^4$ and $R^6$ are as hereinbefore defined) with a compound of formula

(IX)

followed by removal of any carboxyl blocking group $R^6$, and where necessary the separation of syn and anti isomers.

The acids of formula (III) may be converted into the corresponding acid halides and anhydrides and acid addition salts by conventional methods, for example as described hereinabove.

The starting materials of formula (IV) may be prepared by methods analogous to those described in British Pat. No. 1474519 and U.S. Pat. No. 3976546. Alternatively they may be prepared by acylating the corresponding 7-amino-3-hydroxymethyl compounds, for example, analogously to process (A) above.

It should be appreciated that in some of the above transformations it may be necessary to protect any sensitive groups in the molecule of the compound in question to avoid undesirable side reactions. For example, during any of the reaction sequences referred to above it may be necessary to protect the $NH_2$ group of the aminothiazolyl moiety, for example by tritylation, acylation (e.g. chloroacetylation or formylation), protonation or other conventional method. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water, or, in the case of a chloroacetyl group, by treatment with thiourea.

Carboxyl blocking groups used in the preparation of compounds of formula (I) or in the preparation of necessary starting materials are desirably groups which may readily be split off at a suitable stage in the reaction sequence, conveniently at the last stage. It may, however, be convenient in some instances to employ non-toxic metabolically labile carboxyl blocking groups such as acyloxy-methyl or -ethyl groups (e.g. acetoxymethyl or -ethyl or pivaloyoxymethyl) or alkoxycarbonyloxyalkyl groups (e.g. ethoxycarbonyloxyethyl) and retain these in the final product to give an appropriate ester derivative of a compound of formula (I).

Suitable carboxyl blocking groups are well known in the art, a list of representative blocked carboxyl groups being included in British Patent No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form, in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

If desired, such powder formulations may contain an appropriate non-toxic base in order to improve the water-solubility of the active ingredient and/or to ensure that when the powder is reconstituted with water, the pH of the resulting aqueous formulation is physiologically acceptable. Alternatively the base may be present in the water with which the powder is reconstituted. The base may be, for example, an inorganic base such as sodium carbonate, sodium bicarbonate or sodium acetate, or an organic base such as lysine or lysine acetate.

The compositions may also be presented in a form suitable for absorption by the gastro-intestinal tract, for example, tablets, capsules, syrups or suspensions for oral administration, and suppositories.

Compositions for veterinary medicine may, for example, be formulated as intramammary preparations in either long acting or quick-release bases.

The compositions may contain from 0.1% upwards, e.g. 0.1–99% of the active material, depending on the method of administration. When the compositions comprise dosage units, each unit will preferably contain 100–3000 mg of the active ingredient e.g. 200–2000 mg. The daily dosage for adult human treatment will preferably range from 200 to 12000 mg e.g. 1000–9000 mg per day, depending inter alia on the nature of the infection and the route and frequency of administration. In general, intravenous or intramuscular administration will be employed, for example using 400 to 4000 mg per day of the active ingredient in adult human treatment. In treating Pseudomonas infections higher daily doses may be required. It will be appreciated that in some circumstances, for example, in the treatment of neonates, smaller dosage units and daily dosages may be desirable.

The antibiotic compounds according to the invention may be administered in combination with other therapeutic agents such as antibiotics, for example penicillins or other cephalosporins.

The following Examples illustrate the invention. All temperatures are in °C. Sorbsil U30 is silica gel manufactured by Joseph Crosfield and Son of Warrington, Lancashire, England. DMSO is dimethylsulphoxide.

Preparation 1

Ethyl (Z)-2-Cyclopropylmethoxyimino-2-(2-tritylaminothiazol-4-yl)acetate

Ethyl (Z)-2-hydroxyimino-2-(2-tritylaminothiazol-4-yl)acetate, hydrochloride salt (30 g) was stirred with cyclopropylmethyl bromide (13.5 g) in dimethylsulphoxide (150 ml) containing potassium carbonate (30 g) under nitrogen at 21° for 7 hours. The mixture was partitioned between methylene chloride and water. The aqueous layer was extracted with more methylene chloride and the combined organic solutions were washed with water. After drying with magnesium sulphate, the solution was concentrated and loaded onto a column of Sorbsil U30 silica gel (200 g). The column was eluted with ethyl acetate (10 to 30%) in petroleum ether (b.p. 40°–60°). Evaporation of appropriate fractions gave the title compound (20.9 g); $\lambda_{max}$ (ethanol) 234.5 nm ($E_1\ cm^{1\%}$ 403); $\lambda_{inf.}$ 254.5 nm ($E_1\ cm^{1\%}$ 302), 259.5 nm ($E_1\ cm^{1\%}$ 267), 265 nm ($E_1\ cm^{1\%}$ 229), 271.5 nm ($E_1\ cm^{1\%}$ 190) and 294 nm ($E_1\ cm^{1\%}$ 111); $\nu_{max}$ (CHBr$_3$) 3398 (NH), 1730 (ester), and 1593 and 1491 cm$^{-1}$ (aromatic double bond).

Preparation 2

(Z)-2-Cyclopropylmethoxyimino-2-(2-tritylaminothiazol-4-yl)acetic acid

The product of Preparation 1 (20 g) was dissolved in ethanol (200 ml) and sodium hydroxide (3.12 g) in water (40 ml) was added. The mixture was refluxed for 45 minutes during which precipitation occurred. Some of the ethanol (ca 150 ml) was distilled off and the residue was cooled. The mixture was partitioned between methylene chloride and water containing 2N hydrochloric acid (70 ml). The organic layer was washed with water, each aqueous layer being back-extracted with more methylene chloride. The combined organic layers were dried with magnesium sulphate and evaporated to give the title compound (20 g); $\lambda_{inf.}$ (ethanol) 234.5 nm ($E_1\ cm^{1\%}$ 383) 259.5 nm ($E_1\ cm^{1\%}$ 242), 266.5 nm ($E_1\ cm^{1\%}$ 266) and 272.5 nm ($E_1\ cm^{1\%}$ 217); $\nu_{max}$ (Nujol) 3260 (NH) and 1685 cm$^{-1}$ (acid).

Preparation 3

(a) (6R,7R)-3-(N-Methylcarbamoyloxymethyl)-7-(thien-2-yl)acetamidoceph-3-em-4-carboxylic acid A solution of (6R,7R)-3-hydroxymethyl-7-(thien-2-yl)acetamidoceph-3-em-4-carboxylic acid (3.54 g) in dry N,N-dimethylformamide (150 ml) was stirred at 0° to 5° and treated with triethylamine (2.8 ml) and then methyl isocyanate (5.0 ml). The solution was stirred at 4° for 3.25 hours, then poured into 3% sodium bicarbonate solution (1.0 l) which was washed with ethyl acetate. The aqueous portion was covered with ethyl acetate and the pH lowered to 2.0 with orthophosphoric acid. The layers were separated and the aqueous portion further extracted with ethyl acetate. The organic extracts were washed with 0.5N hydrochloric acid and saturated brine, dried and evaporated to give the title acid (1.39 g); $\nu_{max}$ (Nujol) 3420 and 3270 (NH), 2600 and 1728 ($CO_2H$), 1760 ($\beta$-lactam), 1702 and 1530 cm$^{-1}$ (CONH); $\tau$(DMSO-$d_6$) 0.81 (d, J9 Hz, NH), ca 2.50 (aromatic protons), 4.24 (dd, J5 and 9 Hz, C7-H), 6.16 (s, $CH_2$CONH), 6.41 (C2-$CH_2$) and 7.37 (d, J5 $\overline{H}z$, $CH_3NH$).

(b) Diphenylmethyl (6R,7R)-3-(N-methylcarbamoyloxymethyl)-7-(thien-2-yl)acetamidoceph-3-em-4-carboxylate A suspension of (6R,7R)-3-(N-methylcarbamoyloxymethyl)-7-(thien-2-yl)acetamidoceph-3-em-4-carboxylic acid (2.0 g) in tetrahydrofuran (50 ml) was stirred at 20° and a solution of diphenyldiazomethane in dichloromethane (15 ml, 0.28M) was added. The mixture was stirred at 20°. More diphenyldiazomethane in dichloromethane (1.0 ml, 1.44M) was added after 2 hours and again after a further hour. After a total of 4 hours the reaction mixture was evaporated. The residue was triturated with diethyl ether, stirred and filtered. The solid was washed with a little diethyl ether and dried to give the title compound (2.75 g); $\nu_{max}$ (Nujol) 3354 and 3310 (NH), 1790 ($\beta$-lactam), 1704 and 1536 (NHCO$_2$R), 1656 and 1536 cm$^{-1}$ (amide); $\tau$ (DMSO-$d_6$) 0.78 (d, J9 Hz, $CH_2$CONH), ca. 2.2 to ca. 2.9 (thienyl+diphenyl protons+NH$\overline{C}$H$_3$), 3.00 (s, $C\underline{H}(C_6H_5)_2$), and 7.39 (d, J5 Hz, NH$\overline{C}$H$_3$).

EXAMPLE 1

(a) Diphenylmethyl (6R,7R)-3-Carbamoyloxymethyl-7-[(Z)-2-cyclopropylmethoxyimino-2-(2-tritylaminothiazol-4-yl)acetamido]-ceph-3-em-4-carboxylate Oxalyl chloride (0.37 ml) was added to a solution of N,N-dimethylformamide (0.38 ml) in methylene chloride (10 ml) at −20° with stirring. After five minutes at 0°, the mixture was recooled to −20° and (Z)-2-cyclopropylmethoxyimino-2-(2-tritylaminothiazol-4-yl)acetic acid (1.94 g) was added. The solution was stirred at 0° for ten minutes before recooling to −20°. A slurry of diphenylmethyl (6R,7R)-7-amino-3-carbamoyloxymethylceph-3-em-4-carboxylate (1.76 g) in methylene chloride (10 ml) containing N,N-dimethylaniline (1.26 ml) was added. The solution was allowed to warm to 21° and was stirred for 1.5 hours. After dilution with methylene chloride, the solution was washed with dilute hydrochloric acid and water, each time back-extracting with methylene chloride. The combined organic layers were dried (magnesium sulphate) and concentrated. The solution was loaded into a column of Sorbsil U30 (70 g) which was eluted with a gradient of ethyl acetate (10 to 100%) in petroleum ether (b.p. 40°–60°). Evaporation of the appropriate eluate gave the title compound (3.03 g) as a foam, $[\alpha]_D^{21}$+10.7° (c 1.03, CHCl$_3$); $\nu_{infl}$ 238.5 nm (E$_{1\ cm}^{1\%}$ 2.78), 258.5 (E$_{1\ cm}^{1\%}$ 227), 264.5 (E$_{1\ cm}^{1\%}$ 212), 271.5 (E$_{1\ cm}^{1\%}$ 186) and 296.5 (E$_{1\ cm}^{1\%}$ 88)

(b) (6R,7R)-7-[(Z)-2-(2-Aminothiazol-4-yl)-2-cyclopropylmethoxyiminoacetamido]-3-carbamoyloxymethylceph-3-em-4-carboxylic acid, trifluoroacetate salt The compound of stage (a) (2.86 g) was dissolved in anisole (6 ml) and trifluoroacetic acid (24 ml) was added at 21° with stirring. After 1.25 hours, water (1.5 ml) was added. After five minutes the solution was evaporated to half-volume and diisopropyl ether (ca 100 ml) was added. The precipitate was collected by filtration, washed with diisopropyl ether and dried in air. This solid was dissolved in formic acid (7 ml) and water (3 ml) was added. After 1.5 hours, the solution was evaporated to an oil which was triturated with diisopropyl ether to give the title compound (1.50 g), $[\alpha]_D^{21}$+34.1° (c 0.7, chloroform); $\nu_{max}$ 235 nm (E$_{1\ cm}^{1\%}$ 308); $\lambda_{infl}$ 249.5 nm (E$_{1\ cm}^{1\%}$ 281) and 293.5 nm (E$_{1\ cm}^{1\%}$ 117).

EXAMPLE 2

(a) (6R,7R)-7-[(Z)-2-Cyclopropylmethoxyimino-2-(2-tritylaminothiazol-4-yl)acetamido]-3-hydroxymethyl-ceph-3-em-4-carboxylic Acid Oxalyl chloride (0.50 ml) was added under nitrogen to a solution of N,N-dimethylformamide (0.48 ml) in dichloromethane (13 ml) at −20°. The mixture was stirred at 0° for 10 minutes and cooled to −20°. (Z)-2-Cyclopropylmethoxyimino-2-(2-tritylaminothiazol-4-yl)acetic acid (2.528 g) was added and the solution was stirred at 0° for 20 minutes. This solution was added to a solution of (6R,7R)-7-amino-3-hydroxymethylceph-3-em-4-carboxylic acid (1.110 g) in industrial methylated spirits (20 ml), water (2 ml) and triethylamine (5 ml) at 0°. This mixture was stirred at 0° for 30 minutes and evaporated. The solid was stirred with water (20 ml), ethyl acetate (20 ml) and methyl isobutyl ketone (20 ml). The pH of this mixture was adjusted to 3.0 with 20% aqueous phosphoric acid. The solid was washed with water, ethyl acetate, then ether and was dried to give the title acid containing 0.67 moles of triethylamine (1.736 g); $[\alpha]_D^{20}$+39° (c 0.7 in DMSO); u.v. (ethanol) had $\lambda_{max}$ 238 nm (E$_{1\ cm}^{1\%}$ 327) and $\lambda_{infl}$ 259 nm (E$_{1\ cm}^{1\%}$ 250).

(b) (6R,7R)-3-Carbamoyloxymethyl-7-[(Z)-2-cyclopropylmethoxyimino-2-(2-tritylaminothiazol-4-yl)acetamido]-ceph-3-em-4-carboxylic Acid, Sodium Salt A solution of chlorosulphonyl isocyanate (150 mg) in acetone (1 ml) at −10° was added to a solution of the product of Preparation 3 (565 mg) in acetone (5 ml) at −20° under nitrogen. After 15 minutes the suspension was stirred at 0°. After 1 hour a solution of chlorosulphonylisocyanate (150 mg) in ethyl acetate (1 ml) was added and the mixture was stirred for a further hour. A further portion of chlorosulphonyl isocyanate (150 mg) was added followed by water (1 ml) at 0°. The suspension was stirred at 10° to 20° for 1 hour to give a solution, the pH of which was adjusted to 2.5 by the addition of aqueous sodium hydroxide solution. The resulting solution was extracted with ethyl acetate which was washed, dried with sodium sulphate and concentrated to give a solid (62 mg) which was filtered off and a filtrate which was evaporated to give a foam (0.47 g). Part (0.42 g) of the foam in acetone (10 ml) was stirred with a solution of sodium 2-ethylhexanoate (0.57 ml of 1M solution diluted to 2 ml) to give the title compound as a powder (225 mg), u.v. had inflections at 236 nm ($E_1\ _{cm}^{1\%}$ 333) and 259 nm ($E_1\ _{cm}^{1\%}$ 255).

(c)
(6R,7R)-7-[(Z)-2-(2-Aminothiazol-4-yl)-2-cyclopropylmethoxyiminoacetamido]-3-carbamoyloxymethylceph-3-em-4-carboxylic Acid A solution of the product of stage (a) above (136 mg) in formic acid (1.5 ml) was diluted with water (0.5 ml) and stirred at 20° for 1 hour. The mixture was filtered and the solid was washed with a mixture of formic acid and water (3:1). The filtrate was evaporated to give a gum which was triturated with ether to give the title acid (74 mg); u.v. (ethanol) had $\lambda_{max}$ 237 nm ($E_1\ _{cm}^{1\%}$ 321) and $\lambda_{infl}$ 257 nm ($E_1\ _{cm}^{1\%}$ 256); $\nu_{max}$ (Nujol) 3700 to 2500 (NH$_2$,NH,OH and water), 1768 ($\beta$-lactam), 1710 (CO$_2$H and carbamate) and 1660 and 1530 cm$^{-1}$ (amide).

EXAMPLE 3

(a)
(6R,7R)-3-Carbamoyloxymethyl-7-[(Z)-2-cyclopropylmethoxyimino-2-(2-tritylaminothiazol-4-yl)acetamido]-ceph-3-em-4-carboxylic Acid Oxalyl chloride (0.37 ml.) was added to a solution of N,N-dimethylformamide (0.38 ml) in methylene chloride (10 ml) with stirring under nitrogen at −20°. After ten minutes with ice water cooling, the mixture was recooled to −20° and (Z)-2-cyclopropylmethoxyimino-2-(2-tritylaminothiazol-4-yl)acetic acid (1.94 g) was added and the solution was stirred with ice-water cooling for 10 minutes. The solution was recooled to −20° and added to a solution of (6R,7R)-7-amino-3-carbamoyloxymethylceph-3-em-4-carboxylic acid (1.09 g) in industrial methylated spirits (12 ml) and water (3 ml) containing triethylamine (2.4 ml) at −10° and with vigorous stirring. After five minutes, the solution was partitioned between water and methylene chloride. Dilute hydrochloric acid was added to adjust the aqueous layer to pH >2. The aqueous layer was extracted with more methylene chloride and the combined organic layers were washed with water, dried with magnesium sulphate and evaporated. The residue was triturated with diethyl ether to give the title compound (2.32 g); $[\alpha]_D^{21}$+15.88° (c 0.69, CHCl$_3$); $\nu_{max}$ (Nujol) 3540 to 3100 (NH, NH$_2$, OH, and water), 1785 ($\beta$-lactam), 1720 (acid and carbamate) and 1683 and 1510 cm$^{-1}$ (amide).

(b) 1-Acetoxy-1-ethyl (6R,7R)-3-carbamoyloxymethyl-7-[(Z)-2-cyclopropylmethoxyimino-2-(2-tritylaminothiazol-4-yl)acetamido]-ceph-2-em-4-carboxylate (6R,7R)-3-Carbamoyloxymethyl-7-[(Z)-2-cyclopropylmethoxyimino-2-(2-tritylaminothiazol-4-yl)acetamido]ceph-3-em-4-carboxylic acid (1.1 g) was stirred with potassium carbonate (105 mg) in N,N-dimethylformamide (5 ml) with ice water cooling under nitrogen. After five minutes, 1-acetoxy-1-ethyl bromide (300 mg) was added. After one hour at ice-bath temperature and 2.5 hours at 21°, the mixture was partitioned between ethyl acetate and aqueous hydrochloric acid. The aqueous layer was extracted with more ethyl acetate and the combined organic layers were washed with brine, dried with magnesium sulphate and evaporated to a foam. This was chromatographed on Sorbsil U30 (50 g) in ethyl acetate (10 to 70%) in petroleum ether (bp 40°-60°) to give the title compound (840 mg); $\nu_{max}$ (CHBr$_3$) 3583, 3403 (NH and NH$_2$), 1785 ($\beta$-lactam), 1730 (ester and carbamate) and 1688 and 1513 cm$^{-1}$ (amide); $\tau$ (CDCl$_3$) includes 3.04 (NH and OCHCH$_3$), 3.22 (thiazole proton), 4.19 and 4.70 (7-H and 6-H), 4.8 to 5.6 (3CH$_2$ and NH$_2$), and 5.90 (—CH$_2$O).

(c) 1-Acetoxy-1-ethyl (1S, 6R,7R)-3-carbamoyloxymethyl-7-[(Z)-2-cyclopropylmethoxyimino-2-(2-tritylaminothiazol-4-yl)acetamido]-ceph-3-em-4-carboxylate,1-oxide The product of stage (b) (2.7 g) was stirred with 3-chloroperbenzoic acid (734 mg) in methylene chloride (20 ml) with ice-water cooling for 30 minutes. The solution was washed with aqueous sodium bicarbonate solution and water, each time back extracting with further methylene chloride. The combined organic layers were dried with magnesium sulphate and concentrated. The residue was purified by chromatography on Sorbsil U30(50 mg) in ethyl acetate-petroleum ether (bp 40° to 60°) (1:1), then neat ethyl acetate to give the title compound (2.26 g); $[\alpha]_D^{21}$+47.7° (c 0.75, CHCl$_3$). $\nu_{max}$ (Nujol) 3700–3100 (NH and NH$_2$), 1789 ($\beta$-lactam), 1729 (ester), 1705 (carbamate), 1698 and 1520 (amide) and 1069 cm$^{-1}$ (sulphoxide).

(d) 1-Acetoxy-1-ethyl (6R,7R)-3-Carbamoyloxymethyl-7-[(Z)-2-cyclopropylmethoxyimino-2-(2-tritylaminothiazol-4-yl)acetamido]-ceph-3-em-4-carboxylate The product of Stage (c) (2.1 g) was dissolved in N,N-dimethylformamide (35 ml) and potassium iodide (1.63 g) was added with stirring and ice-water cooling. Acetyl chloride (0.35 ml) was added. After about 1 hour, more acetyl chloride (0.17 ml) was added. After a further 30 minutes the solution was partitioned between ethyl acetate and aqueous sodium metabisulphite solution. The aqueous layer was extracted with further ethyl acetate and the combined organic layers were washed successively with dilute hydrochloric acid and brine (twice). After drying with magnesium sulphate, the solution was concentrated and chromatographed on Sorbsil U30 (50 g) in ethyl acetate (50 to 70%) in petroleum ether (b.p. 40°-60°) to give the title compound (1.73 g); $[\alpha]_D^{21}$+23.1° (c 1.1, CHCl$_3$); $\nu_{max}$ (CHBr$_3$) 3540,3403 (NH and NH$_2$), 1791 ($\beta$-lactam), 1752 and 1732 (esters) 1720 (carbamate) and 1689 and 1517 cm$^{-1}$ (amide).

(e) 1-Acetoxy-1-ethyl (6R,7R)-7-[(Z)-2-(2-Aminothiazol-4-yl)-2-cyclopropylmethoxyiminoacetamido]-3-carbamoyloxymethylceph-3-em-4-carboxylate 1-Acetoxy-1-ethyl (6R,7R)-3-carbamoyloxymethyl-7-[(Z)-2-cyclopropylmethoxyimino-2-(2-tritylaminothiazol-4-yl)acetamido]ceph-3-em-4-carboxylate (1.5 g) was dissolved in formic acid (15 ml) and water (7.5 ml) was added. After 1.5 hour at 21°, the mixture was filtered and the filter-cake was leached with formic acid-water (2:1). The combined filtrates were concentrated and the residue was mixed with isopropanol when a solution formed. This was evaporated to dryness and the residue was partitioned between ethyl acetate and aqueous sodium bicarbonate solution. The aqueous layer was extracted with more ethyl acetate and the combined organic layers were washed with brine and dried with magnesium sulphate. After evaporation, the residue was triturated with isopropanol (5 ml) to give the title compound (540 mg); $[\alpha]_D^{21}+17.9°$ (c 1.2, CHCl$_3$); $\lambda_{max}$ (ethanol) 238.5 nm (E$_{1\ cm}^{1\%}$ 287), $\lambda_{infl}$ 256 nm (E$_{1\ cm}^{1\%}$ 249) and $\lambda_{infl}$ 280 nm (E$_{1\ cm}^{1\%}$ 179).

EXAMPLE 4

(a) 1-Ethoxycarbonyloxy-1-ethyl (6R,7R)-3-Carbamoyloxymethyl-7-[(Z)-2-cyclopropyl-methoxyimino-2-(2-tritylaminothiazol-4-yl)acetamido]-ceph-3-em-4-carboxylate (6R,7R)-3-Carbamoyloxymethyl-7-[(Z)-2-cyclopropylmethoxyimino-2-(2-tritylaminothiazol-4-yl)acetamido]ceph-3-em-4-carboxylic acid (1.1 g) was dissolved in N,N-dimethylformamide (5 ml) and stirred with potassium carbonate (105 mg) under nitrogen with ice-water cooling. After 10 minutes, 1-ethoxycarbonyloxy-1-ethyl bromide was added. After one hour, the mixtured was allowed to attain 21° and was stirred thus for three hours. The mixture was partitioned between ethyl acetate and aqueous hydrochloric acid. The aqueous layer was extracted with more ethyl acetate and the combined organic layers were washed twice with brine, dried with magnesium sulphate and concentrated. The residue was chromatographed on Sorbsil U30 (50 g) in ethyl acetate (10 to 60%) in petroleum ether (bp 40° to 60°) to give the title compound (930 mg); $[\alpha]_D^{21}+44.0°$ (c 1.30, CHCl$_3$); $\lambda_{max}$ (ethanol) 230 nm (E$_{1\ cm}^{1\%}$312), $\lambda_{infl}$ 236 nm (E$_D^{1\%}$295) and $\lambda_{nm}$ (E$_{1\ cm}^{1\%}$226).

(b) 1-Ethoxycarbonyloxy-1-ethyl (6R,7R)-7-[(Z)-2-(2-aminothiazol-4-yl)-2-cyclopropyl-methoxyiminoacetamido]-3-carbamoyloxymethylceph-3-em-4-carboxylate The product from stage (a) (810 mg) was dissolved in formic acid (8 ml) and water (4 ml) was added with stirring at 21°. After 1.25 hours the precipitate was removed by filtration and the filter-cake was leached with formic acid-water (2:1). The combined filtrates were concentrated and the residue was triturated with diethyl ether to give the title compound (340 mg); $[\alpha]_D^{21}+56.35°$ (c 1.3, CHCl$_3$+1 drop DMSO); $\nu_{max}$ (Nujol) 3700–3100 (NH$_2$+NH), 1768 ($\beta$-lactam), 1722 (ester), 1704 (carbamate), and 1678 and 1535 cm$^{-1}$ (amide).

EXAMPLE 5

(a) Diphenylmethyl (6R,7R)-7-[(Z)-2-cyclopropylmethoxyimino-2-(2-tritylaminothiazol-4-yl)acetamido]-3-N-methylcarbamoyloxymethyl)ceph-3-em-4-carboxylic acid A solution of diphenylmethyl (6R,7R)-3-(N-methylcarbamoyloxymethyl)-7-(thien-2-yl)acetamidoceph-3-em-4-carboxylate (500 mg) in methylene chloride (26 ml) was cooled to 5° under nitrogen, and pyridine (0.11 ml) was added, followed by phosphorus pentachloride (0.28 g). The mixture was stirred at 5° for 1.5 hours and more phosphorus pentachloride (51 mg) and pyridine (0.02 ml) were added. After stirring for a further 30 minutes, the mixture was transferred at 5° to a solution of butan-1,3-diol (0.87 ml) in methylene chloride (8.7 ml), also at 5° under nitrogen. The solution was stirred at 5° for 40 minutes, and water (8.7 ml) was added. The mixture was stirred at 10° for 50 minutes, and the organic layer was then separated. The aqueous phase was extracted with more methylene chloride. The combined organic layers were dried and concentrated to a small volume, to give a solution of diphenylmethyl (6R,7R)-7-amino-3-(N-methylcarbamoyloxymethyl)ceph-3-em-4-carboxylate (solution A).

Oxalyl chloride (0.09 ml) was added to a solution of N,N-dimethylformamide (0.09 ml) in methylene chloride (2.3 ml), at −20°. The mixture was stirred at −20° for 1 minute and then in an ice-bath for 10 minutes before recooling to −20°. (Z)-2-Cyclopropylmethoxyimino-2-(2-tritylaminothiazol-4-yl)acetic acid (440 mg) was added and the solution was stirred in an ice-bath for 10 minutes before recooling to −20° (solution B). Solution A (ca.5 ml) was treated with N,N-dimethylaniline (0.28 ml) and added rapidly to solution B at −20°. The mixture was stirred at 0° for 10 minutes and then allowed to warm to room temperature. After stirring at room temperature for 30 minutes, the reaction mixture was diluted with dichloromethane and washed with 2N aqueous hydrochloric acid and then with water. The organic layer was separated, dried and evaporated to leave a crude product. This was chromatographed on silica gel in a mixture of ethyl acetate and petroleum ether (40°–60°) to give the title ester as a foam (0.413 g); $[\alpha]_D+28.6°$ (c 1.05; DMSO); $\nu_{max}$ (CHBr$_3$) 3456 and 3400 (NH), 1790 ($\beta$-lactam), 1728 (ester), 1688 (OCONHCH$_3$), 1683 and 1516 (amide) and 753 and 739 cm$^{-1}$ (Phenyl).

(b) (6R,7R)-7-[(Z)-2-(2-Aminothiazol-4-yl)-2-cyclopropylmethoxyiminoacetamido]-3-(N-methylcarbamoyloxymethyl)ceph-3-em-4-carboxylic acid The product of stage (a) (0.34 g) was dissolved in trifluoroacetic acid (3.6 ml) and stirred at 5° for 5 minutes and then at room temperature for 35 minutes. The solution was diluted with diisopropyl ether. The resulting solid was collected by filtration, washed with diisopropyl ether and dried. This was dissolved in 98% formic acid (2 ml) and water (1.0 ml) was added. After stirring for 30 minutes, the resulting precipitate was filtered and the filter-cake was washed with a formic acid and water mixture. The filtrate was concentrated and diisopropyl ether was added. The resulting solid was then collected, washed with diisopropyl ether and dried to leave the title compound as a solid (93 mg); $[\alpha]_D+25.0°$ (c 0.60; DMSO); $\nu_{max}$ (Nujol) 3700 to 2100 (NH+NH$_3^+$+OH), 1776 ($\beta$-lactam), 1660 and 1543 (amide) and 1720 to 1600 cm$^{-1}$ (OCONHCH$_3$+CO$_2^-$+CO$_2$H).

EXAMPLE A

Dry Powder For Injection

Fill sterile (6R,7R)-7-[(Z)-2-(2-aminothiazol-4-yl)-2-cyclopropylmethoxyiminoacetamido]-3-carbamoylmethylceph-3-em-4-carboxylic acid, sodium salt aseptically into glass vials, such that each vial contains an amount equivalent to 1.0 g of the antibiotic acid. Purge the vial headspaces with sterile nitrogen and close the vials using rubber discs or plugs, and metal overseals applied by crimping. Constitute the product shortly before administration by dissolving in Water for Injections or other suitable sterile vehicle.

The above sodium salt may be prepared in conventional manner, for example by reacting the compound of Example 2 with an appropriate base.

Example B

| Dry Powder for Injection | |
| --- | --- |
| (6R,7R)-7-[(Z)-2-(2-aminothiazol-4-yl)-2-cyclopropylmethoxyiminoacetamido]-3-carbamoyloxymethylceph-3-em-4-carboxylic acid | 1.00 g |
| Sodium carbonate (anhydrous) | 0.140 g |

Mix the sterile cephalosporin antibiotic aseptically with the sodium carbonate in a powder blender. Fill the blend aseptically into glass vials, such that each vial contains an amount equivalent to 500 mg of the cephalosporin antibiotic. Purge the vial headspaces with sterile nitrogen and close the vials using rubber discs or plugs, and metal overseals applied by crimping. Constitute the product shortly before administration by dissolving in Water for Injections or other suitable sterile vehicle.

I claim:

1. Cephalosporin antibiotics having a formula

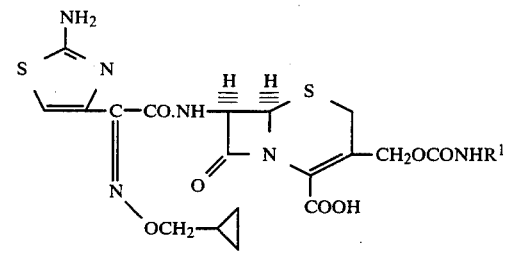

wherein $R^1$ represents a hydrogen atom or a methyl or 2-chloroethyl group and non-toxic salts and nontoxic metabolically labile esters thereof.

2. A compound according to claim 1 which is (6R,7R)-7-[(Z)-2-(2-aminothiazol-4-yl)-2-cyclopropylmethoxyiminoacetamido]-3-carbamoyloxymethylceph-3-em-4-carboxylic acid and non-toxic salts thereof.

3. Non-toxic metabolically labile esters of the compounds of claim 1.

4. A pharmaceutical composition comprising as active ingredient, an antibacterially effective amount of a compound according to claim 1 in association with a pharmaceutical carrier or excipient.

5. A compound according to claim 1 which is (6R,7R)-7-[(Z)-2-(2-aminothiazol-4-yl)-2-cyclopropylmethoxyiminoacetamido]-3-carbamoyloxymethylceph-3-em-4-carboxylic acid and non-toxic metabolically labile esters thereof.

* * * * *